(12) United States Patent
Grodzki et al.

(10) Patent No.: US 10,132,900 B2
(45) Date of Patent: *Nov. 20, 2018

(54) METHOD AND APPARATUS FOR MAGNETIC RESONANCE EXAMINATION OF AN EXAMINATION OBJECT

(71) Applicant: Siemens Aktiengesellschaft, Munich (DE)

(72) Inventors: David Grodzki, Erlangen (DE); Rene Kartmann, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 474 days.

This patent is subject to a terminal disclaimer.

(21) Appl. No.: 14/838,609

(22) Filed: Aug. 28, 2015

(65) Prior Publication Data

US 2016/0061922 A1 Mar. 3, 2016

(30) Foreign Application Priority Data

Aug. 29, 2014 (DE) ........................ 10 2014 217 284

(51) Int. Cl.
| | |
|---|---|
| *G01V 3/00* | (2006.01) |
| *G01R 33/56* | (2006.01) |
| *G01R 33/58* | (2006.01) |
| *G01R 33/48* | (2006.01) |
| *A61B 5/055* | (2006.01) |
| *G01R 33/50* | (2006.01) |
| *G01R 33/563* | (2006.01) |

(52) U.S. Cl.
CPC .......... *G01R 33/5608* (2013.01); *A61B 5/055* (2013.01); *G01R 33/4828* (2013.01); *G01R 33/50* (2013.01); *G01R 33/5601* (2013.01); *G01R 33/56341* (2013.01); *G01R 33/583* (2013.01)

(58) Field of Classification Search
USPC ........................................................ 324/309
See application file for complete search history.

(56) References Cited

U.S. PATENT DOCUMENTS

| | | | |
|---|---|---|---|
| 2004/0142496 A1* | 7/2004 | Nicholson .............. | A61B 5/055 436/536 |
| 2012/0235678 A1* | 9/2012 | Seiberlich .............. | G01R 33/56 324/307 |

(Continued)

OTHER PUBLICATIONS

Ma et al., "Magnetic Resonance Fingerprinting", Nature, 495, 187-192 (Mar. 14, 2013).

*Primary Examiner* — Rodney Fuller
(74) *Attorney, Agent, or Firm* — Schiff Hardin LLP

(57) ABSTRACT

In a method and apparatus for magnetic resonance examination of an examination object, in order to determine a substance by execution of a magnetic resonance fingerprinting procedure for examination of an examination object in which a substance is located, a magnetic resonance signal waveform of a voxel of an examination area of the examination object is acquired by a magnetic resonance fingerprinting recording procedure, and a signal comparison of the magnetic resonance signal waveform is made in a computer with a substance signal waveform stored in a database, and the result of the signal comparison is provided as an output from the computer.

7 Claims, 3 Drawing Sheets

(56) References Cited

U.S. PATENT DOCUMENTS

| | | | |
|---|---|---|---|
| 2013/0265047 A1* | 10/2013 | Griswold | G01R 33/56 324/309 |
| 2015/0005243 A1* | 1/2015 | O'Day | G01N 33/5038 514/23 |
| 2016/0033604 A1* | 2/2016 | Grodzki | G01R 33/4828 324/309 |
| 2016/0097830 A1* | 4/2016 | Grodzki | A61B 5/055 324/309 |
| 2016/0282434 A1* | 9/2016 | Seiberlich | G01R 33/50 |
| 2016/0291105 A1* | 10/2016 | Knoll | A61B 6/4417 |
| 2017/0108566 A1* | 4/2017 | Fenchel | G01R 33/4828 |

* cited by examiner

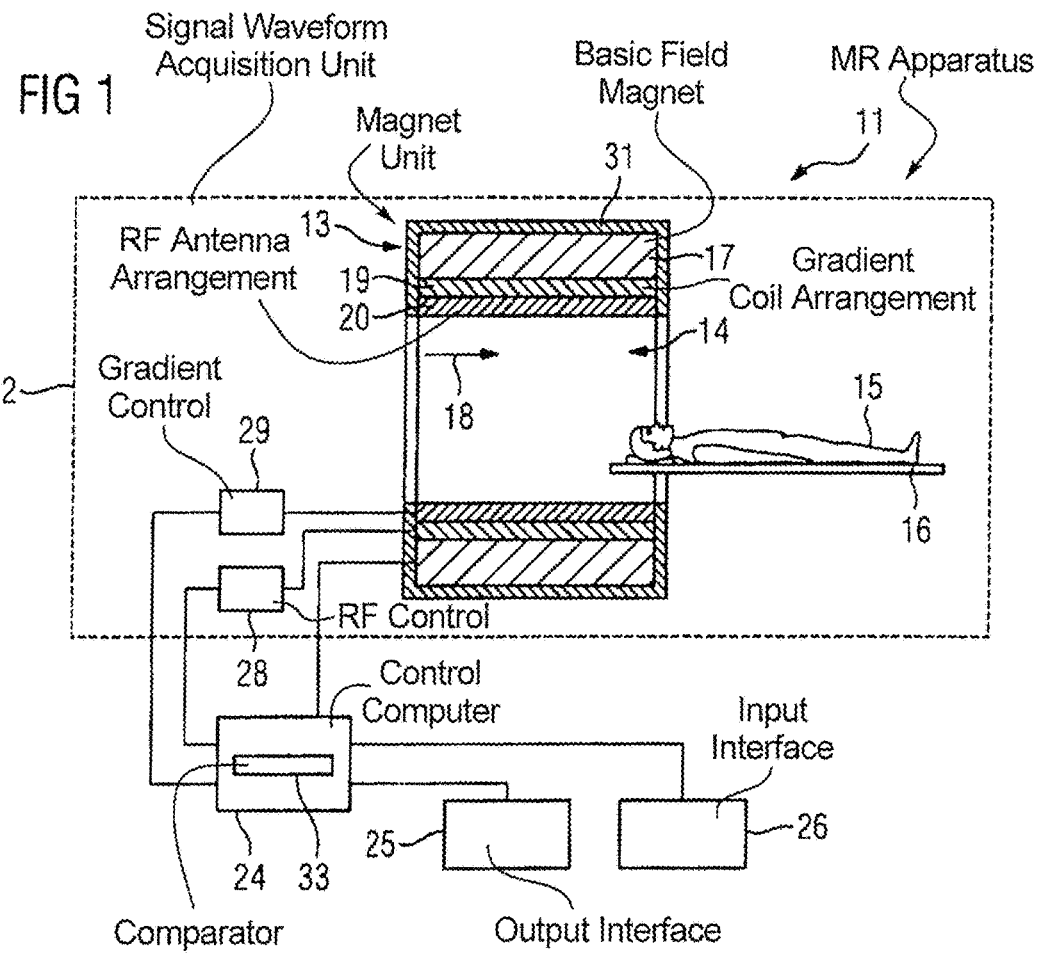
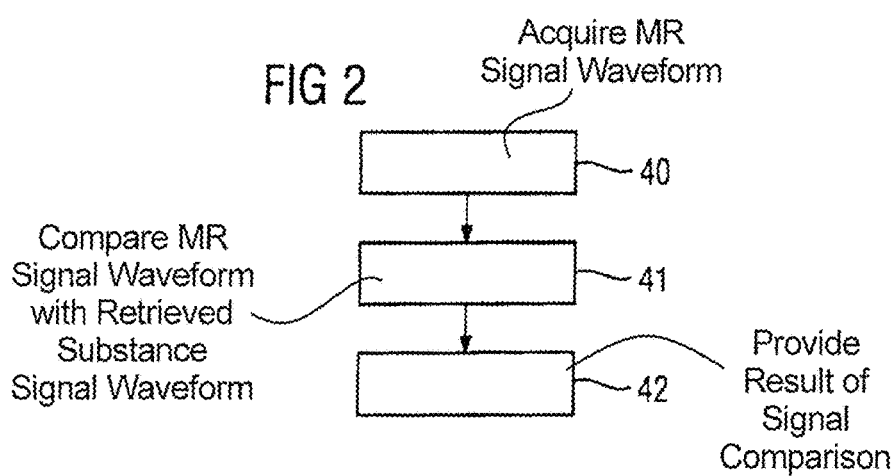

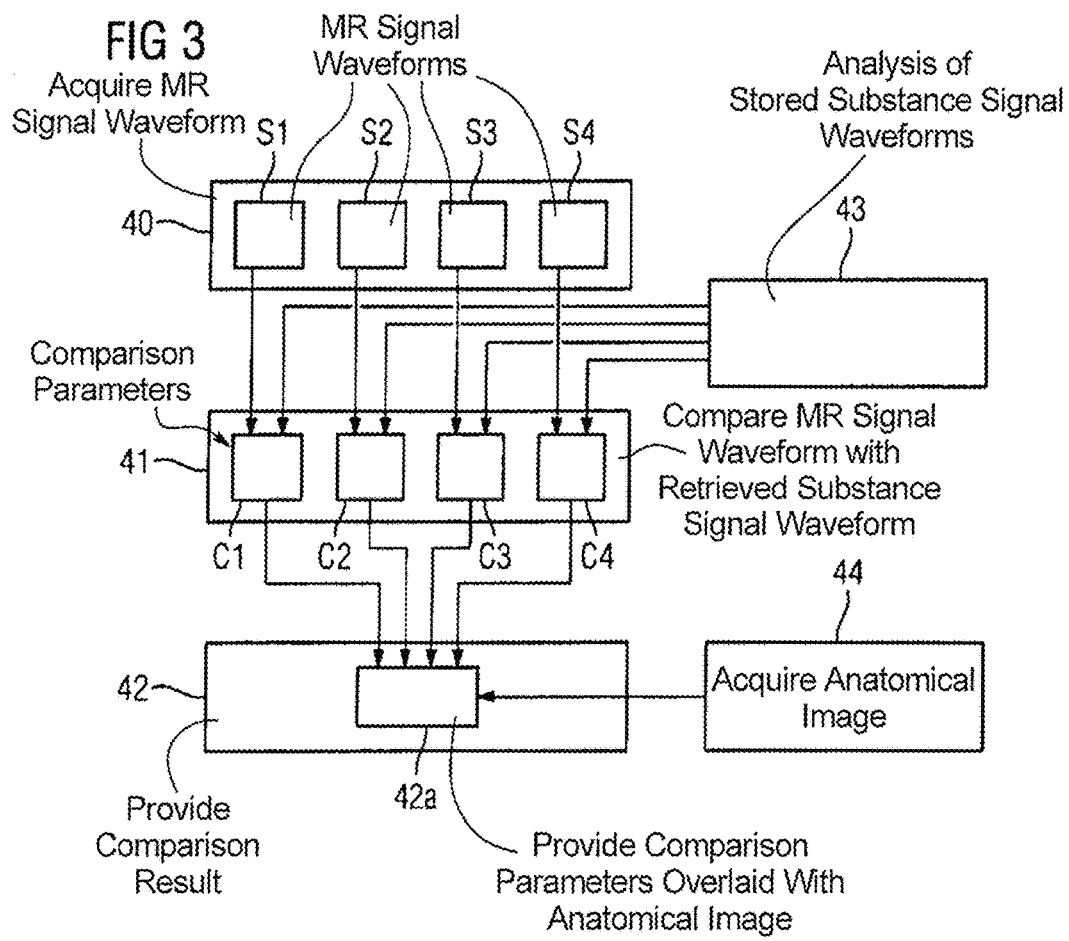

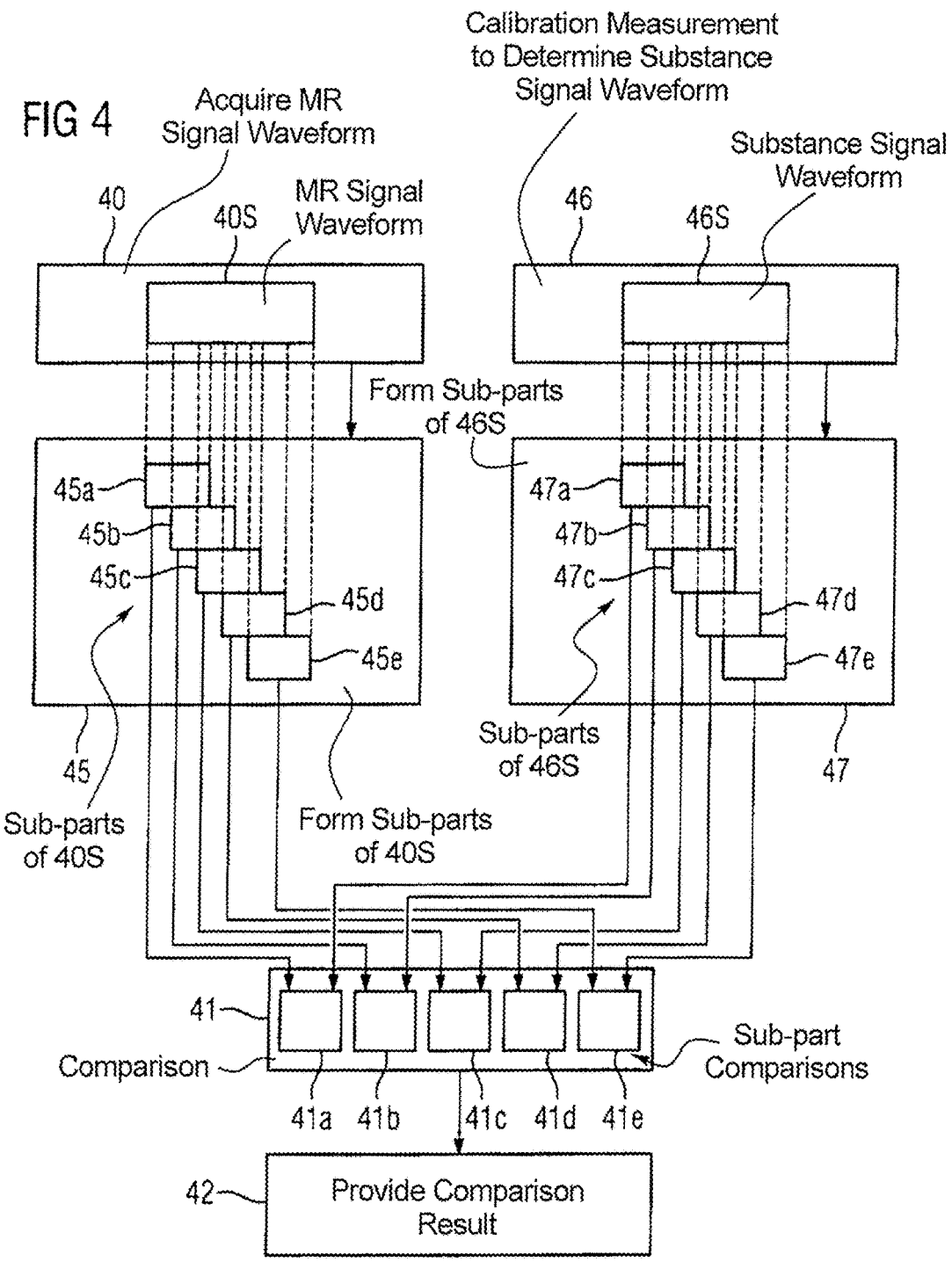

METHOD AND APPARATUS FOR MAGNETIC RESONANCE EXAMINATION OF AN EXAMINATION OBJECT

BACKGROUND OF THE INVENTION

Field of the Invention

The invention concerns a method for magnetic resonance examination of an examination object and to a magnetic resonance apparatus for implementing such a method.

Description of the Prior Art

In a magnetic resonance apparatus, also called a magnetic resonance tomography system, the body of a person to be examined, such a patient, is usually exposed, with the use of a basic field magnet, to a relatively strong magnetic field, of 1.5 or 3 or 7 Tesla for example. In addition, gradient pulses are emitted with the use of a gradient system. Radio frequency (RF) pulses, particularly excitation pulses, are then emitted by a radio-frequency system via suitable antennas, which causes nuclear spins of specific atoms that excited resonantly by these high RF pulses to be flipped by a defined flip angle in relation to the magnetic field lines of the basic magnetic field. During the relaxation of the nuclear spins, radio-frequency signals, so called magnetic resonance signals, are emitted that are received by suitable radio frequency antennas and then further processed. From the raw data of an examination volume acquired in this way, the desired magnetic resonance image data of the examination volume can be reconstructed.

Magnetic resonance imaging can serve to determine the presence and/or distribution of a substance that is located in the examination object. The substance may be specific tissue of the examination object, such as tissue that is suspected to be pathological, a contrast medium, or a marking substance. In such cases it is known that a segmentation of magnetic resonance image data recorded (acquired) by the magnetic resonance apparatus can be undertaken with respect to the substance (i.e., substance-containing image regions cab be segmented).

A magnetic resonance fingerprinting method is known from the document Ma et al., "Magnetic Resonance Fingerprinting", Nature, 495, 187-192 (14 Mar. 2013).

SUMMARY OF THE INVENTION

An object of the invention is to provide an effective method for determining the presence of a substance by a magnetic resonance fingerprinting method.

A method for magnetic resonance (MR) examination of an examination object according to the invention, wherein a substance is located in the examination object, includes the following steps.

A magnetic resonance signal waveform of a voxel of an examination area of the examination object is acquired by operating an MR apparatus, in particular the MR scanner, thereof, to execute a magnetic resonance fingerprinting data acquisition procedure.

A signal comparison of the magnetic resonance signal waveform is then made with a substance signal waveform that is stored in a database.

A result of the signal comparison is then made available as an electronic signal.

The examination object can be a patient, a training person or a phantom. The substance is located in the examination area even before the beginning of the acquisition of the magnetic resonance signal waveform. Thus, inter alia, magnetic resonance signals emitted by the substance are included in the magnetic resonance signal waveform.

The substance can be a contrast medium for the magnetic resonance imaging. The substance can also be formed by tissue of the examination object, for example brain tissue, bone tissue, fatty tissue, muscle tissue, blood tissue etc. The substance can also be formed by pathological tissue of the examination object, for example tumor tissue or inflammation tissue. Furthermore, the substance can also be a marking substance, which is used for marking a further substance and/or tissue. Naturally the substance can also be embodied in a different way, as appears meaningful to those skilled in the art.

A signal waveform, such as e.g. the MR signal waveform or the substance signal waveform generally comprises a change of an MR signal over time. The MR signal waveform can therefore describe the change of the acquired MR signal during the course of the MR fingerprinting data acquisition. The magnetic resonance signal waveform specifies how the signal value of a voxel of the recorded magnetic resonance signal changes during the acquisition of the magnetic resonance signal waveform. The voxel in this case specifies the area from which the magnetic resonance signal waveform is acquired. It is also possible for the magnetic resonance signal waveform to be acquired from an area that is more coarsely resolved than a voxel. Then the magnetic resonance signal waveform can be acquired as an average over a number of voxels for example. A time resolution of the magnetic resonance signal waveform in such cases is embodied by a temporal spacing of the recording of different magnetic resonance signals. The magnetic resonance fingerprinting recording method can include different recording parameters that are set for the acquisition of the various magnetic resonance signals. The recording parameters in such cases can be varied in a pseudo-randomized way. Thus the acquired magnetic resonance signal waveform can exhibit a pseudo-randomized waveform. Possible recording parameters that are changed during the acquisition of the magnetic resonance signal waveform are, for example, the echo time, the design and/or number of radio frequency pulses, the design and/or number of gradient pulses, a diffusion encoding etc. In this way a magnetic resonance signal waveform that is characteristic for the voxel, a so-called fingerprint of the voxel can be acquired by execution of the magnetic resonance fingerprinting recording procedure.

The substance signal waveform especially represents the magnetic resonance signal waveform to be expected during the magnetic resonance fingerprinting recording method when a sample of the substance is examined. The substance waveform, as described below, can be established, for example, in a calibration method and/or simulated. As an alternative, the substance signal waveform can be determined on the basis of known material properties of the substance. The signal comparison of the magnetic resonance signal waveform with the substance signal waveform can include a determination of the similarity between the magnetic resonance signal waveform and the substance signal waveform. The similarity in this case can be established in a correlation analysis, for example. Naturally further procedures for signal comparison appearing meaningful to those skilled in the art are also conceivable. The substance signal waveform can be loaded from the database for the signal comparison.

The provision of the result of the signal waveform can include a display of the result on a display monitor and/or storage of the result in a database.

The inventive method of operation is based on the insight that, for an explicit determination of a presence of a substance by magnetic resonance fingerprinting, a signal comparison of the magnetic resonance signal waveform with the substance signal waveform, which is assigned to the substance, can be sufficient. In a conventional magnetic resonance fingerprinting method, a number of database signal waveforms, which are respectively assigned different values of at least one tissue parameter, are stored in the database. The number of database signal waveforms can be very large in such cases if a number of tissue parameters are to be defined and/or the tissue parameters are to be defined in a precisely individualized way. For example, if two tissue parameters are to be defined by means of a conventional magnetic resonance fingerprinting method, for example a T1 relaxation time and a T2 relaxation time, in a graduation of 1 ms in a range of values from in each case 0 to 2000 ms, then the database will typically include more than 4,000,000 database signal waveforms. Thus, in accordance with a conventional magnetic resonance fingerprinting method, a complicated signal comparison of the magnetic resonance signal waveform with the number of database signal waveforms must be carried out.

This complicated signal comparison can be dispensed with in the inventive process, since the acquired magnetic resonance signal waveform can be explicitly compared with the substance signal waveform. If a number of substances are to be identified and/or a distinction is to be made between different substances, the magnetic resonance signal waveform can also be compared to a number of substance signal waveforms. However the number of substance signal waveforms is then still restricted, such as to a maximum of 15, preferably to a maximum of 10 and most preferably to a maximum of 5. As already described, a signal comparison of the magnetic resonance signal waveform with an individual substance signal waveform can be undertaken. The database signal waveforms are then restricted to the single substance signal waveform or to a number of substance signal waveforms. The database signal waveforms are restricted in this way such as to a maximum of 15, preferably to a maximum of 10 and most preferably to a maximum of 5. The restriction of the database signal waveforms is based in this case on the selected substance that is to be searched for. The substance signal waveform in this case, as described below, can be determined by a calibration measurement and/or a suitable restriction of a conventional magnetic resonance fingerprinting database. Thus the inventive process advantageously has a greatly reduced comparison database compared to that of a conventional magnetic resonance fingerprinting method, which contains those signal waveforms with which the acquired magnetic resonance signal waveform is compared. The method step of signal comparison thus can be carried out with reduced computing outlay. Thus a presence of the substance can be determined especially efficiently.

The inventive method, unlike a conventional magnetic resonance fingerprinting method, thus advantageously does not deliver any distribution of quantitative values of the at least one tissue parameter. Instead the result of the signal comparison that is provided can contain information as to the extent to which the acquired magnetic resonance signal waveform correlates with the substance signal waveform. In this way, the presence of the substance in the examination area can be determined especially advantageously. Above all in this case an explicit tuning (customization) of the inventive method to a specific substance is possible. The substance to be determined can in such cases be pre-specified by a user via an input interface and/or from a measurement protocol.

At the same time the inventive method makes use of the fact that the magnetic resonance signal waveform acquired by the magnetic resonance fingerprinting recording method can be compared with a substance signal waveform that is characteristic for the substance, i.e., the fingerprint of the substance. On the basis of the characteristic magnetic resonance fingerprinting recording method, in a further correlation of the magnetic resonance signal waveform with the substance signal waveform, the substance can be identified with a high degree of certainty. If the magnetic resonance signal waveform differs markedly from the substance signal waveform it can be assumed that the magnetic resonance signal waveform was acquired from tissue that is different from the substance sought. Thus a unique determination of the presence of the substance in the voxel is possible by the inventive method.

In an embodiment, the signal comparison of the magnetic resonance signal waveform with the substance signal waveform includes the determination of a comparison parameter between the magnetic resonance signal waveform and the substance signal waveform, and the provision of the result of the signal comparison includes provision of the comparison parameter. An especially advantageous comparison parameter is a correlation coefficient, which can be determined in the signal comparison in a correlation analysis between the magnetic resonance signal waveform and the substance signal waveform. It is also possible to determine the comparison parameter based on a frequency spectrum of the magnetic resonance signal waveform and the spectrum of the substance signal waveform to be determined. As an alternative or in addition, the signal comparison can be based on a wavelet transformation. Naturally further comparison parameters that appear meaningful to those skilled in the art are also conceivable. The comparison parameter can provide especially informative quantitative information for the determination of a presence of the substance. The comparison parameter can also be provided in binary form. Thus a threshold value for the comparison parameter can be set and it can be defined whether the established comparison parameter lies above the threshold or not. Information about a presence of the substance can be provided especially easily in this way.

In another embodiment, multiple magnetic resonance signal waveforms are acquired from a number of voxels of the examination area, and the signal comparison includes a determination of multiple comparison parameters between the multiple magnetic resonance signal waveforms and the substance signal waveform, and the provision of the result of the signal comparison is a provision of a spatially-resolved distribution of the multiple comparison parameters. To detect the multiple magnetic resonance signal waveforms, multiple magnetic resonance raw images are acquired. The acquisition of the multiple magnetic resonance raw images of the examination area typically includes, for each magnetic resonance raw image of the multiple magnetic resonance raw images, acquisition of multiple spatially-resolved magnetic resonance signal values. These signal values are in an image area of the examination area. The signal values especially do not occur in k-space. The magnetic resonance raw images in this case are typically not intended to be displayed to an observer. The multiple magnetic resonance raw images in this case can be acquired during multiple repetition times, wherein in each case one magnetic resonance raw image of the multiple magnetic raw images can be acquired during one repetition time of the number of repetition times. Thus the number of magnetic resonance raw images is preferably recorded following on from one another in time, especially in a defined time frame. Each magnetic resonance raw image in this case has an identical recording volume (Field of View, FoV). Thus the multiple magnetic resonance raw images represent a temporal development of the recorded magnetic resonance signals in the examination area. A number of spatially-dependent magnetic resonance signal waveforms are then generated over the multiple magnetic resonance raw images. In such cases, the different magnetic resonance signal waveforms are preferably generated in each case over corresponding voxels of the number of magnetic resonance raw images. A magnetic resonance signal waveform of the multiple magnetic resonance signal waveforms can thus specify how a signal value of a voxel of the number of voxels changes over the multiple magnetic resonance raw images. Each magnetic resonance signal waveform thus specifies a change of recorded magnetic resonance signal values over the period of acquisition of the number of magnetic resonance raw images. A time resolution of the magnetic resonance signal waveforms in this case is formed by a distance in time between the acquisition of two magnetic resonance raw images of the number of magnetic resonance raw images. Each magnetic resonance signal waveform of the multiple magnetic resonance signal waveforms is then respectively compared with the substance signal waveform, in multiple signal comparisons. In this way it can be established how the number of comparison parameters determined in the multiple signal waveforms change spatially. The spatially-resolved distribution of the substance in the examination area includes information as to the locations in the examination area of which the substance is situated. Thus the spatially-resolved distribution of the substance can provide information, for example, as to how the correlation between the magnetic resonance signal waveform and the substance signal waveform changes spatially. The provision of the location-resolved distribution can include a display of the spatially-resolved distribution for a user, for example on a monitor. As an alternative or in addition, the provision of the spatially-resolved distribution can include storage of the spatially-resolved distribution, for example in a database. The spatially-resolved distribution of the multiple comparison parameters offers an observer differentiated and thus especially advantageous information about the presence of this substance in the examination area.

In another embodiment, the provision of the spatially-resolved distribution of the multiple comparison parameters includes a presentation of the spatially-resolved distribution of the multiple comparison parameters overlaid with an anatomical magnetic resonance image of the examination area. The anatomical magnetic resonance image can have, for example, a T1 weighting or a T2 weighting. The anatomical magnetic resonance image can also be created from the multiple magnetic resonance raw images from which the magnetic resonance signal waveforms are generated. The spatially-resolved distribution can be shown color-coded overlaid with the anatomical magnetic resonance image. Then the anatomical magnetic resonance image is advantageously displayed in grayscale. If the spatially-resolved distribution is displayed in binary form, then those voxels of the anatomical magnetic resonance image in which the substance has been localized can be shown highlighted. The fused representation of the spatially-resolved distribution with the anatomical magnetic resonance image makes an especially rapid assessment possible for an observer as to the locations in the examination area at which the substance is situated.

In another embodiment, the signal comparison includes multiple sub-part signal comparisons, wherein a sub-part signal comparison of the number of part signal comparisons includes a comparison of a section of the magnetic resonance signal waveform with a corresponding section of the substance signal waveform, and the result of the signal comparison is determined time-resolved based on results of the multiple part signal comparisons. Different sections of the signal waveform are in such cases based on different time windows of the acquisition of the magnetic resonance signal waveform. Thus a first section of the magnetic resonance signal waveform can be acquired during a first time window of the duration of the acquisition of the magnetic signal waveform and a second section of the magnetic resonance signal waveform during a second time window of the duration of the acquisition of the magnetic resonance signal waveform. The first time window and the second time window in this case are at least partly different. Corresponding sections of two signal waveforms in this case are preferably those sections of the two signal waveforms that were acquired during the same time window during the acquisition of the magnetic resonance image data. Based on the multiple sub-part signal comparisons of different sections of the magnetic resonance signal waveform and of the substance signal waveform, a time-resolved result of the signal comparison can be determined. The time-resolved result of the signal comparison can include a temporal development of the signal comparison, especially of the comparison parameter over the duration of the acquisition of the magnetic resonance signal waveform. Thus on the basis of a sub-part signal comparison of a first section of the magnetic signal waveform with a corresponding first section of the substance signal waveform, a first comparison parameter can be determined and on the basis of a sub-part signal comparison of a second section of the magnetic resonance signal waveform with the corresponding second section of the substance signal waveform, a second comparison parameter can be determined. The first comparison parameter can then be set for a first time window that is based on the first section and the second comparison parameter can be set for a second time window that is based on the second section. Thus the comparison parameters can be determined time-resolved. In this way, it is possible to determine a time curve of a presence of the substance in the examination area. This is especially advantageous if the substance is non-stationary, for example if the substance includes blood or contrast medium. In this case it is advantageous that the magnetic resonance signal waveform is compared exclusively with the substance signal waveform, because the multiple sub-part signal comparisons can be carried out with reasonable computing outlay. Furthermore, a unique assignment of the magnetic resonance signal waveform to the substance signal waveform is possible, although in each case only sections of the signal waveforms are considered.

In another embodiment, sections of the magnetic resonance signal waveform, which are compared in different part signal comparisons with the corresponding sections of the substance signal waveform, partly overlap. Thus the different sections of the magnetic resonance signal waveforms are not disjoint. In this way a refinement of the time resolution of the time-resolved determination of the result of the signal comparison is possible.

In another embodiment, multiple database signal comparisons are stored in the database, and that database signal waveform of the number of database signal waveforms, which is assigned to the substance, is used as the substance signal waveform for the signal comparison. The database in this case can be embodied as a conventional magnetic resonance fingerprinting database. For use in the inventive method, this database can then advantageously be restricted. The signal of the magnetic resonance signal waveform thus is not compared with all database signal waveforms. Instead, the magnetic resonance signal waveform is compared, exclusively with the substance signal waveform. Thus a pre-selection of the database signal waveforms is made. For this pre-selection the substance to be sought is pre-specified. Based on the pre-specified substance, the substance signal waveform can then be selected from among multiple database signal waveforms. In this case, some of the database signal waveforms may be allocated to markers that make possible an assignment of the database signal waveforms to specific substances. When the specified substance is to be sought, the appropriate database signal waveform then can be set, on the basis of the marker, as the substance waveform.

In another embodiment, each of the multiple database signal waveforms is assigned a database value of at least one tissue parameter, and that database signal waveform among the multiple database signal waveforms for which the assigned database value best correlates with a known substance value of the at least one tissue parameter, is used as the substance signal waveform for the signal comparison. A prerequisite for this is that the substance value of the at least one tissue parameter is known. The substance in such cases has the substance value of the at least one tissue parameter. In this case, material properties of the substance must be known. The database signal waveform represents the signal waveform to be expected in the magnetic resonance fingerprinting method if a sample of which the value of the at least one tissue parameter corresponds to the associated database value is examined. The at least one tissue parameter advantageously characterizes a physical characteristic of a tissue of the examination object from which the magnetic resonance signal waveform was acquired. In particular, the at least one tissue parameter can quantify a reaction of the tissue to a radio-frequency excitation. The at least one tissue parameter can be formed by one or more of the following tissue parameters: T1 relaxation time, T2 relaxation time, a diffusion value (for example an apparent diffusion coefficient, ADC), a magnetization moment, proton density, resonant frequency, concentration of a substance, temperature etc. Naturally further parameters that appear meaningful to those skilled in the art are also conceivable. A number of values of different tissue parameters can also be determined, and any given combination of the tissue parameters is suitable. In this way the substance signal waveform can be selected especially simply from the database signal waveforms. The setting of markers for the database signal waveforms can be dispensed with. Advantageously, only one item of information about the substance value of the at least one tissue parameter is needed in order to determine the substance signal waveform. Thus an existing magnetic resonance fingerprinting database can be reduced to those entries that are assigned the physical characteristics of the substance.

In another embodiment, a calibration measurement, during which the substance signal waveform is measured from a sample of the substance by the magnetic resonance fingerprinting recording method, is executed before the signal comparison, and the substance signal waveform obtained from the calibration measurement is stored in the database. The calibration measurement can be undertaken once, and then all following determinations of distributions of the substance, possibly in different examination objects, can be done on the basis of the one-time calibration measurement. In this case, it is advantageous for a pure sample of the substance to be examined by execution of the magnetic resonance fingerprinting recording method. As an alternative, the substance signal waveform can be determined in a calibration measurement conducted specifically for a particular examination object. For this purpose, before a signal comparison is carried out in an area of the body in which it is known that this substance has accumulated, the substance signal waveform is determined by the magnetic resonance fingerprinting recording method. The magnetic resonance fingerprinting recording method used in the calibration measurement should be the same as the magnetic resonance fingerprinting recording method used for acquiring the magnetic resonance signal waveform. In particular, the recording parameters are varied over time in both measurements in the same way. The presence of the substance thus can be determined in a manner that is tailored to the substance itself Furthermore the invention concerns a magnetic resonance (MR) apparatus with a signal waveform acquisition unit formed as a scanner of the MR apparatus, a provision interface and a computer with a comparator, wherein the computer is designed to implement the inventive method.

The magnetic resonance apparatus thus is embodied for implementing a method for a magnetic resonance examination of an examination object, wherein a substance is located in the examination object. The signal waveform acquisition unit (scanner) is operated to acquire a magnetic resonance signal waveform of a voxel of an examination area of the examination object by execution of a magnetic resonance fingerprinting recording procedure. The comparator makes a signal comparison of the magnetic resonance signal waveform with a substance signal waveform stored in a database. The provision interface is configured to provide the result of the signal comparison as an electronic signal.

In an embodiment of the magnetic resonance apparatus, the comparator and the provision interface are configured such that the signal comparison of the magnetic resonance signal waveform with the substance signal waveform includes a determination of a comparison parameter between the magnetic resonance signal waveform and the substance signal waveform, and the provision of the result of the signal comparison includes a provision of the comparison parameter.

In another embodiment of the magnetic resonance apparatus, the signal waveform acquisition unit, the comparator and the provision interface are configured such that multiple magnetic resonance signal waveforms are acquired from multiple voxels of the examination area, and the signal comparison includes a determination of multiple comparison parameters between the multiple magnetic resonance signal waveforms and the substance signal waveform, and the provision of the results of the signal waveform comparison includes provision of a spatially-resolved distribution of the number of comparison parameters.

In another embodiment of the magnetic resonance apparatus, the provision interface is configured such that the provision of the spatially-resolved distribution of the number of comparison parameters includes a presentation of the spatially-resolved distribution of the multiple comparison parameters overlaid with an anatomical magnetic resonance image of the examination area.

In another embodiment of the magnetic resonance apparatus, the comparator is configured such that the signal comparison includes multiple part signal comparisons, wherein a sub-part signal comparison of the multiple sub-part signal comparisons includes a comparison of a section of the magnetic resonance signal waveform with a corresponding section of the substance signal waveform, and the result of the signal comparison is determined time-resolved based on the results of the multiple sub-part signal comparisons.

In another embodiment of the magnetic resonance apparatus, the comparator is configured such that sections of the magnetic resonance signal waveform, which are compared in different sub-part signal comparisons with the corresponding sections of the substance signal waveform, partly overlap.

In another embodiment of the magnetic resonance apparatus, the comparator is configured such that multiple database signal waveforms are stored in the database, and that signal database waveform among the multiple database waveforms that is assigned to the substance, is used as the substance signal waveform for the signal comparison.

In another embodiment of the magnetic resonance apparatus, the comparator is configured such that each of the multiple database signal waveforms is assigned a database value of at least one tissue parameter, and that database signal waveform among the multiple database signal waveforms of which the assigned database value of the at least one tissue parameter best correlates with a known substance value of the at least one tissue parameter, is used as the substance signal waveform for the signal comparison.

In another embodiment of the magnetic resonance apparatus, the scanner is operated to execute a calibration measurement before the signal comparison, during which the substance signal waveform is measured from a sample of the substance by means of the magnetic resonance fingerprinting recording method, and the substance signal waveform is stored in the database.

The advantages of the inventive magnetic resonance apparatus essentially correspond to the advantages of the inventive method that have been explained in detail above. Features, advantages or alternate forms of embodiment mentioned above are applicable as well to the apparatus. The functional features of the method are embodied by corresponding physical modules, especially by hardware modules in the apparatus.

BRIEF DESCRIPTION OF THE DRAWINGS

FIG. 1 schematically shows an inventive magnetic resonance apparatus.

FIG. 2 is a flowchart of a first embodiment of the inventive method.

FIG. 3 is a flowchart of a second embodiment of the inventive method.

FIG. 4 is a flowchart of a third embodiment of the inventive method.

DESCRIPTION OF THE PREFERRED EMBODIMENTS

FIG. 1 is a schematic illustration of an inventive magnetic resonance (MR) apparatus 11. The magnetic resonance apparatus 11 has a detector unit formed by a magnet unit 13 with a basic field magnet 17 for creating a strong and constant basic magnetic field 18. The scanner of the magnetic resonance apparatus 11 also has a cylindrical patient receiving area 14 for receiving an examination object 15, in the present case a patient 15, wherein the patient receiving area 14 is cylindrically enclosed in the circumferential direction by the magnet unit 13. The patient 15 can be moved by a patient support 16 of the magnetic resonance apparatus 11 into the patient receiving area 14. The patient support 16 has a bed for this purpose, which is movably mounted within the scanner of the magnetic resonance apparatus 11. The magnet unit 13 is shielded outwardly by housing cladding 31.

The magnet unit 13 also has a gradient coil unit 19 for creating magnetic field gradients, which are used for spatial encoding during imaging. The gradient coil arrangement 19 is activated by a gradient control unit 28. Furthermore the magnet unit 13 has a radio-frequency antenna arrangement 20, which is formed in the shown embodiment as a body coil integrated at a fixed location into the magnet unit 13, and a radio-frequency antenna control unit 29 for exciting nuclear spins of the examination object 15 so as to depart from the polarization produced by the basic magnetic field 18 created by the basic field magnet 17. The radio-frequency antenna arrangement 20 is controlled by the radio-frequency antenna control unit 29 and radiates radio-frequency magnetic resonance sequences into an examination area that is essentially formed by the patient receiving area 14. The radio-frequency antenna arrangement 20 is further designed to receive magnetic resonance signals from the patient 15.

To control the basic field magnet 17, the gradient control unit 28 and the radio-frequency antenna control unit 29, the magnetic resonance apparatus 11 has a computer 24. The computer 24 controls the magnetic resonance apparatus 11 centrally, for example, to execute a predetermined imaging gradient echo sequence. Control information such as imaging parameters, and as well as reconstructed magnetic resonance images, can be provided to a user via an output interface 25, in the present case a display monitor 25 of the magnetic resonance apparatus 11. In addition the magnetic resonance apparatus 11 has an input interface 26 via which information and/or parameters can be entered by a user during a measuring 9 (data acquisition) procedure. The computer 24 can include the gradient control unit 28 and/or radio-frequency antenna control unit 29 and/or the display monitor 25 and/or the input interface 26.

The computer 24 includes a comparator 33.

The magnetic resonance apparatus 11 further includes a signal waveform acquisition unit (scanner) 32. The signal waveform acquisition unit 32 is formed in the present case by the magnet unit 13 together with the radio-frequency antenna control unit 29 and the gradient control unit 28. The magnetic resonance apparatus 11 is thus designed, together with the signal waveform acquisition unit 32, the computer 24 and the output interface 25, for implementing the inventive method.

The magnetic resonance apparatus 11 shown can naturally include other components that magnetic resonance devices 11 normally have. The general way in which a magnetic resonance apparatus 11 functions is known to those skilled in the art, so that a detailed description of the further components is not necessary herein.

FIG. 2 is a flowchart for a first embodiment of the inventive method for magnetic resonance examination of an examination object 15, wherein a substance is located in the examination object 15.

In a first method step 40, the signal waveform acquisition unit 32 acquires a magnetic resonance (MR) signal waveform of a voxel of an examination area of the examination object 15 by execution of a magnetic resonance fingerprinting recording method. The magnetic resonance fingerprinting recording method advantageously in this case makes use of pseudo-randomized changed recording parameters during the acquisition of the magnetic resonance signal waveform. The acquired magnetic resonance signal waveform then specifies how a magnetic resonance signal recorded from the voxel changes over a period of acquisition of the magnetic resonance signal waveform.

In a further method step 41 the comparator 33 of the computer 24 carries out a signal comparison of the magnetic resonance signal waveform with a substance signal waveform stored in a database. The signal comparison can be made by a conventional pattern recognition method and/or by a correlation analysis. In the signal comparison, a comparison parameter is emitted as an output that characterizes the degree of correlation between the magnetic resonance signal waveform and the substance signal waveform.

In a further method step 42 the result of the signal comparison is provided by the output interface 25. In the present case, the result of the signal comparison can be displayed on the display monitor. The result of the signal comparison can also be stored. If a comparison parameter is also emitted in the output from the signal comparison, then the comparison parameter is provided as well via the output interface.

FIG. 3 is a flowchart of a second embodiment of the inventive method for magnetic resonance examination of an examination object 15, wherein a substance is located in the examination object 15.

The description below is restricted to the differences from the exemplary embodiment in FIG. 2, wherein, for method steps that remain the same, the description of the exemplary embodiment in FIG. 2 applies. Method steps that essentially remain the same are basically given the same reference numbers.

The second embodiment of the inventive method shown in FIG. 3 includes the method steps 40, 41, 42 of the first embodiment of the inventive method according to FIG. 2. The second embodiment of the inventive method shown in FIG. 3 contains additional method steps and substeps. An alternate method sequence to that shown in FIG. 3 is also conceivable, which has only some of the additional method steps and/or substeps shown in FIG. 2. Naturally an alternate method sequence to that shown in FIG. 3 can also have additional method steps and/or substeps.

In further method step 40, multiple magnetic resonance signal waveforms S1, S2, S3, S4 of multiple voxels of the examination area are acquired by the signal waveform acquisition unit 32. In the present case, for clarity, four magnetic resonance signal waveforms S1, S2, S3, S4 are acquired. For a more precise spatial resolution, however, more than four magnetic resonance signal waveforms S1, S2, S3, S4. The magnetic resonance signal waveforms S1, S2, S3, S4 are acquired at different points in the examination area. The magnetic resonance signal waveforms S1, S2, S3, S4 are preferably acquired at the same time in such cases. For this purpose, multiple magnetic resonance raw images can be acquired after one another in time by the signal waveform acquisition unit 32, from, which then the magnetic resonance signal waveforms S1, S2, S3, S4 will be generated. In the present case, each magnetic resonance raw image has four voxels, which may be disposed in a 2×2 matrix.

In a further method step 43, the substance signal waveform that is to be compared with the magnetic resonance signal waveforms is determined. FIG. 3 shows an exemplary option for determining the substance signal waveforms by a reduction of an existing magnetic resonance fingerprinting database. It is also conceivable for the substance signal waveform to be determined by the method shown in further method step 46 in FIG. 4. Naturally other options for determining the substance signal waveform are also conceivable.

In further method step 43, for determining the substance signal waveform, an analysis of an existing database is performed by the computer 24, namely an existing magnetic resonance fingerprinting database. Stored in the database are multiple database signal waveforms and for the signal comparison in further method step 41, that database signal waveform of the multiple database signal waveforms that is assigned to the substance, is used as the substance signal waveform. In order to determine this database signal waveform, each of the multiple database signal waveforms is assigned a database value of at least one tissue parameter. Then, that database signal waveform of the multiple signal waveforms of which the assigned database value of the at least one tissue parameter best correlates with a known substance value of the at least one tissue parameter, is used as the substance signal waveform.

The signal comparison in further method step 41 includes a determination of multiple comparison parameters C1, C2, C3, C4 between the number of magnetic resonance signal waveforms S1, S2, S3, S4 and the substance signal waveform determined in the further method step 43. In the present case, four signals are compared as an example, wherein one magnetic resonance signal waveform S1, S2, S3, S4 of the four magnetic resonance signal waveforms S1, S2, S3, S4 is compared with the substance signal waveform in each case. Thus four comparison parameters C1, C2, C3, C4 based on the four signal comparison are also determined, for example four correlation coefficients.

In further method step 42, the output interface 25 can then provide the comparison parameters, in the present case a spatially-resolved distribution of the multiple comparison parameters can be provided. It is advantageous, in a further method step 44, for an anatomical magnetic resonance image of the examination area also to be acquired. Then the spatially-resolved distribution of the multiple comparison parameters can namely be displayed in a substep 42a of the further method step 42 overlaid with the anatomical magnetic resonance image.

FIG. 4 shows a flowchart of a third embodiment of the inventive method for magnetic resonance examination of an examination object 15, wherein a substance is located in the examination object 15.

The description given below is essentially restricted to the differences from the exemplary embodiment in FIG. 2, wherein, for method steps which remain the same, the description of the exemplary embodiment in FIG. 2 applies. Method steps which essentially remain the same are given the same reference numbers.

The third embodiment of the inventive method shown in FIG. 4 includes the method steps 40, 41, 42 of the first embodiment of the inventive method in accordance with FIG. 2. The third embodiment of the inventive method shown in FIG. 4 contains additional method steps and substeps. An alternate method sequence to that shown in FIG. 4 is also conceivable, which has only some of the additional method steps and/or substeps shown in FIG. 2. Naturally an alternate method sequence to that shown in FIG. 4 can also have additional method steps and/or substeps.

In a further method step 46, the substance signal waveform that is to be compared with the magnetic resonance signal waveforms is determined. FIG. 4 shows an exemplary option for determining the substance signal waveform by a calibration measurement. It is also conceivable for the substance signal waveform to be determined by the further method step 43 of the method shown in FIG. 3. Naturally further options for determining the substance signal waveform are also conceivable.

In the exemplary embodiment shown in FIG. 4, a calibration measurement is made in further method step 46 before the signal comparison. During the calibration measurement the substance signal waveform 46S is measured from a sample of the substance by means of the magnetic resonance fingerprinting recording method. Subsequently the substance signal waveform 46S is stored in the database.

Furthermore, in a further method step 45*a*, a number of sections (sub-parts) 45*a*, 45*b*, 45*c*, 45*d*, 45*e* of the magnetic resonance signal waveform 40S are formed by the computer 24 from the magnetic resonance signal waveform 40S acquired in the further method step 40. In the present case, five sections (sub-parts) 45*a*, 45*b*, 45*c*, 45*d*, 45*e* of the magnetic resonance signal waveform 40S are formed, wherein naturally a different number of sections 45*a*, 45*b*, 45*c*, 45*d*, 45*e* of the magnetic resonance signal waveform 40S can also be formed. In the present case the sections 45*a*, 45*b*, 45*c*, 45*d*, 45*e* of the magnetic resonance signal waveform 40S partly overlap.

In the same way multiple sections 47*a*, 47*b*, 47*c*, 47*d*, 47*e* of the substance signal waveform 46S are formed by the computer 24 from the substance signal waveform in a further method step 47. The sections 47*a*, 47*b*, 47*c*, 47*d*, 47*e* of the substance signal waveforms 46S are formed in this case such that they correspond to the sections 45*a*, 45*b*, 45*c*, 45*d*, 45*e* of the magnetic resonance signal waveform 40S. Thus the first section 47*a* of the substance signal waveform 46S corresponds to the first section 45*a* of the magnetic resonance signal waveform 40S, etc.

The further method step 41 has multiple sub-part signal comparisons 41*a*, 41*b*, 41*c*, 41*d*, 41*e*. In these sub-part signal comparisons 41*a*, 41*b*, 41*c*, 41*d*, 41*e*, a comparison of one section 45*a*, 45*b*, 45*c*, 45*d*, 45*e* of the magnetic resonance signal waveform 40S with a corresponding section 47*a*, 47*b*, 47*c*, 47*d*, 47*e* of the substance signal waveform 46S occurs. For example, the first section 45*a* of the magnetic resonance signal waveform 40S is compared with the first section 47*a* of the substance signal waveform 46S etc. The result of the signal comparison is then determined time-resolved, based on results of the multiple sub-part signal comparisons 41*a*, 41*b*, 41*c*, 41*d*, 41*e*, and is presented in a time-resolved manner in further method step 42. For example, a comparison parameter, which can be shown time-resolved, can be determined in each of the multiple sub-part signal comparisons 41*a*, 41*b*, 41*c*, 41*d*, 41*e*. The number of sections 45*a*, 45*b*, 45*c*, 45*d*, 45*e* of the magnetic resonance signal waveform 40S, and the degree of overlapping of the sections 45*a*, 45*b*, 45*c*, 45*d*, 45*e* of the magnetic resonance signal waveform 40S typically determine the time resolution of the time-resolved determination of the result.

The exemplary embodiment shown in FIG. 4 thus results in a time-resolved determination of the presence of the substance in the examination area. The time-resolved determination can be combined with the spatially-resolved determination described in FIG. 3. For this purpose, the method steps 40, 45, 41, 42 shown in FIG. 4 are repeated for multiple magnetic resonance signal waveforms 40S acquired from different voxels.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance (MR) method for detecting whether a substance is present in a subject, comprising:
   using a computer to generate and emit control signals to an MR scanner that cause said MR scanner to execute an MR fingerprinting data acquisition method, so as to obtain a respective MR signal waveform from each of a plurality of voxels of an examination area of the subject;
   in a processor, receiving an input that designates said substance, and retrieving a substance signal waveform from a database in which the substance signal waveform is stored, said substance signal waveform being a signal waveform that is expected to be emitted by said substance in said MR fingerprinting data acquisition method;
   in said processor, for each voxel in said plurality of voxels, making a signal comparison of the respective signal waveform obtained therefrom with the retrieved substance signal waveform so as to obtain a comparison result dependent on a similarity between the respective MR signal waveform and said substance signal waveform, said comparison result designating whether said substance is present in that voxel;
   using said computer to generate and emit control signals to said MR scanner that cause said MR scanner to obtain an anatomical image of said examination area, said MR image also comprising said plurality of voxels of the examination area;
   in said processor, generating a spatially-resolved distribution of the respective comparison results for each voxel in the examination area, which shows respective individual voxels in said examination area in which said substance is present; and
   at a display monitor in communication with said processor, displaying said spatially-resolved distribution of the respective comparison parameters overlaid on said anatomical image of said examination area.

2. A method as claimed in claim 1 comprising generating, as said comparison result, a comparison parameter that quantifies said similarity, and including a designation of said comparison parameter in said electronic signal.

3. A method as claimed in claim 1 comprising, in said processor, dividing said MR signal waveform into a plurality of MR signal waveform sub-parts, and dividing said retrieved substance signal waveform into a plurality of retrieved substance signal waveform sub-parts, and comparing the respective MR signal waveform sub-parts with the respective retrieved signal waveform sub-parts in a plurality of respective sub-part comparisons, and generating said comparison result as a time-resolved comparison result compiled from said plurality of sub-part comparisons.

4. A method as claimed in claim 1 wherein the respective MR signal waveform sub-parts and the respective retrieved substance signal waveform sub-parts that are respectively compared with each other in the respective sub-part comparisons overlap partially with each other.

5. A method as claimed in claim 1 comprising assigning the different database signal waveforms respectively to different substances by assigning a respectively different tissue parameter to each of the database signal waveforms in said database, and retrieving, as said retrieved substance signal waveform, the database signal waveform among said plurality of database signal waveforms that has a tissue parameter assigned thereto that best correlates with a known tissue parameter of the substance in said object.

6. A method as claimed in claim 1 comprising generating said substance signal waveform in a calibration measurement made before said signal comparison, and storing said substance signal waveform from said calibration measurement in said database.

7. A magnetic resonance (MR) apparatus that detects whether a substance is present in a subject, said MR apparatus comprising:

an MR scanner;

a computer configured to generate and emit control signals to an MR scanner that cause said MR scanner to execute an MR fingerprinting data acquisition method, so as to obtain a respective MR signal waveform from each of a plurality of voxels of an examination area of the subject;

said computer being configured to receive an input that designates said substance, and retrieving a substance signal waveform from a database in which the substance signal waveform is stored, said substance signal waveform being a signal waveform that is expected to be emitted by said substance in said MR fingerprinting data acquisition method;

for each voxel in said plurality of voxels, said computer being configured to make a signal comparison of the respective signal waveform obtained therefrom with the retrieved substance signal waveform so as to obtain a comparison result dependent on a similarity between the respective MR signal waveform and said substance signal waveform, said comparison result designating whether said substance is present in that voxel;

said computer being configured to generate and emit control signals to said MR scanner that cause said MR scanner to obtain an anatomical image of said examination area, said MR image also comprising said plurality of voxels of the examination area;

said computer being configured to generate a spatially-resolved distribution of the respective comparison results for each voxel in the examination area, which shows respective individual voxels in said examination area in which said substance is present; and a display monitor in communication with said computer; and said computer being configured to display said spatially-resolved distribution of the respective comparison parameters at said display, overlaid on said anatomical image of said examination area at said display.

\* \* \* \* \*